United States Patent [19]

Cronin

[11] Patent Number: 4,695,382
[45] Date of Patent: Sep. 22, 1987

[54] COMBINED FLUID FILTER AND DELIVERY TUBING

[75] Inventor: James J. Cronin, Mission Viejo, Calif.

[73] Assignee: Microgon, Inc., Laguna Hills, Calif.

[21] Appl. No.: 799,318

[22] Filed: Nov. 18, 1985

[51] Int. Cl.⁴ ............................................. B01D 13/00
[52] U.S. Cl. ................................ 210/436; 210/500.23; 604/406
[58] Field of Search .................. 55/159; 210/436, 927, 210/500.23; 604/406

[56] References Cited

U.S. PATENT DOCUMENTS 4,568,366 2/1986 Frederick et al. ............... 210/436 X Primary Examiner—Frank Spear
Attorney, Agent, or Firm—Paul R. Wylie

[57] ABSTRACT

According to this invention, there has been provided an inline final filter unit for the filtration and administration of intravenous fluids or the like wherein a flexible, nonporous intravenous tubing member contains microporous hollow fibres arranged within the tubular member parallel to the longitudinal direction of such tubing. The fibres are closed at one end and open at the opposite end. A flow blocking material is arranged around the fibres for blocking fluid flow through the flexible tubular member, other than through the material of said hollow fibres. At least one gas permeable hydrophobic fibre is arranged to extend into the tubing member in proximity to the microporous hollow filter fibres. One end of the hydrophobic fibre(s) is in communication with the atmosphere.

13 Claims, 5 Drawing Figures

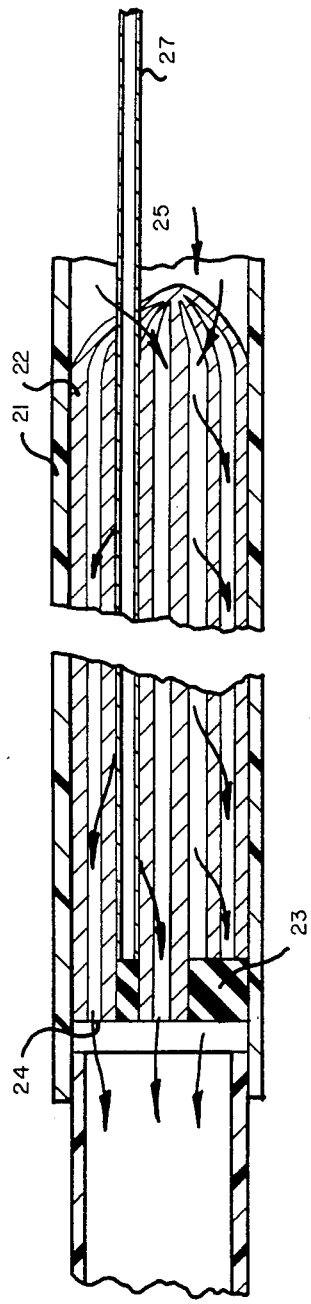
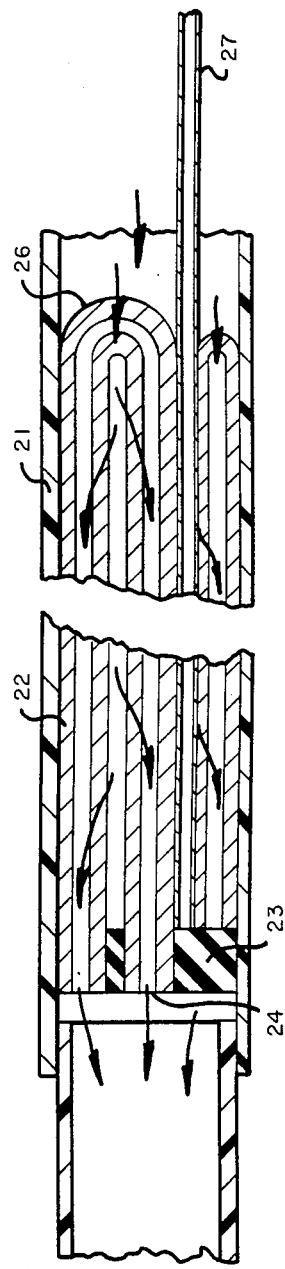
FIG. 4
FIG. 4A

COMBINED FLUID FILTER AND DELIVERY TUBING

BACKGROUND OF THE INVENTION

This invention relates to an inline final filter and more particularly to such a filter which can be combined, and form a part of, fluid tubing for administration of fluids such as intravenous fluids. The invention also relates to a method of manufacturing such a filter.

It has been conventional practice to filter intravenous as well as other parenteral solutions prior to the administration of such solutions to a patient. The purpose of such filtration has been to remove particulate matter and bacteria that may be present.

In recent years, there has been an attempt to place filtration units inline in the administration apparatus so that the fluids are filtered as they are being administered. Example of such inline units include those disclosed in U.S. Pat. No. 4,066,556 to Vaillancourt. It has been found however that these inline filtration units present problems in that they are bulky and expensive to manufacture.

According to this invention, there is provided a combined inline final filter and/or tubing unit for the filtration and administration of fluids which overcome the difficulties of the prior art and represents an advancement in the state of art by efficiently providing filtration in an inline filter that may be no bulkier than the administration tubing itself, will be easy to prime, and will prevent air blockage irrespective of position.

SUMMARY

According to this invention, there has been provided an inline final filter unit for the filtration and administration of intravenous fluids or the like wherein a flexible, nonporous intravenous tubing member contains microporous hollow fibres arranged within the tubular member parallel to the longitudinal direction of such tubing. The fibres are closed at one end and open at the opposite end. A flow blocking material is arranged around the fibres for blocking fluid flow through the flexible tubular member, other than through the material of said hollow fibres.

At least one gas permeable hydrophobic fibre is arranged to extend into the tubing member and proximity to the microporous hollow filter fibres. One end of the hydrophobic fibre(s) is in communication with the atmosphere. In a preferred form of the invention, the hydrophobic fibre is potted in one arm of a "Y" connection in the tubing assembly.

It was an object of this invention to provide an inline final filter that would be simple to manufacture, flexible, utilize standard parts, and be capable of easy packaging and use.

It was a further object of this invention to provide a means of filtration which could utilize existing intravenous administration tubing.

It was a further object of this invention to provide a filter which would allow all entrained air to be easily vented thereby having a very short primary time and being easy to prime.

It was a still further object of this invention to provide a filter from which entrained air could be removed independent of position.

Further objects of this invention will be evident from the following description.

DESCRIPTION OF THE DRAWINGS

The invention will be more fully understood and described with reference to the drawings wherein:

FIGS. 4 and 4A are enlarged fragmentary views similar to FIG. 2 showing details of the invention.

DETAILED DESCRIPTION OF THE INVENTION

Figure 1:
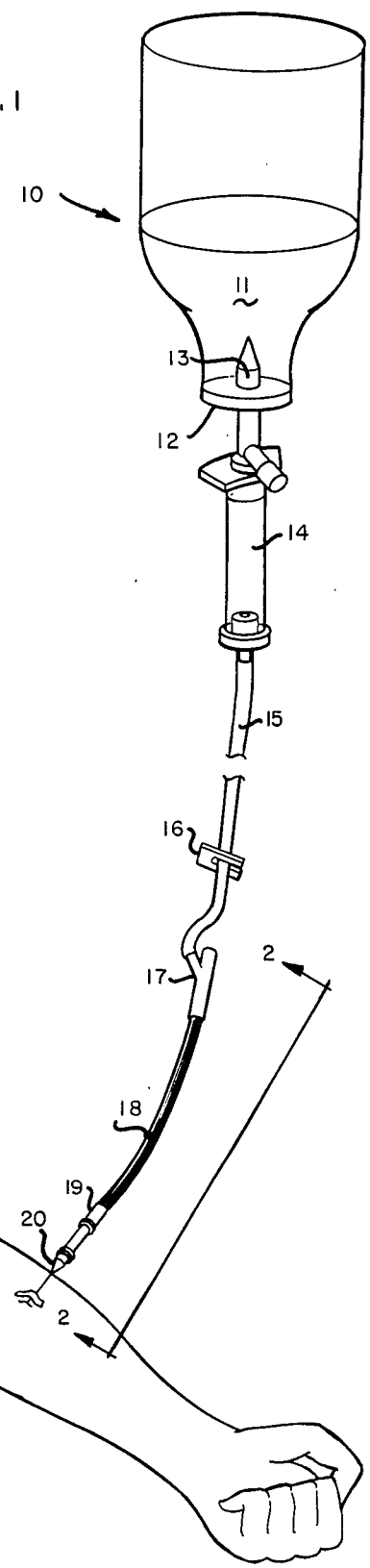
FIG. 1 is a view in perspective of an intravenous administration set incorporating the filter of the invention and showing the administration of fluids to a patient.

As shown in FIG. 1, an administration set which comprises the inline final filter according to the invention includes an I.V. fluid container 10 which contains an I.V. fluid 11 and has a closure 12. A spike 13 runs through closure 12 to provide an outlet for the I.V. fluid into a drip chamber 14, of conventional design. A flexible administration tube 15 is attached to drip chamber 14. Clamp 16 can be provided for controlling the flow of the I.V. fluid 11 through tube 15. At its other end, tube 15 is connected by means of a "Y" fitting 17 the final filter unit 18 according to the invention and as will hereinafter be more fully described. Filter unit 18 in turn is connected by a second coupling 19 to injection needle 20 which is inserted into the vein of a patient. Alternatively, additional tubing, and/or appliances including "Y" filterings may be connected downstream from filter unit 18.

Figure 2:
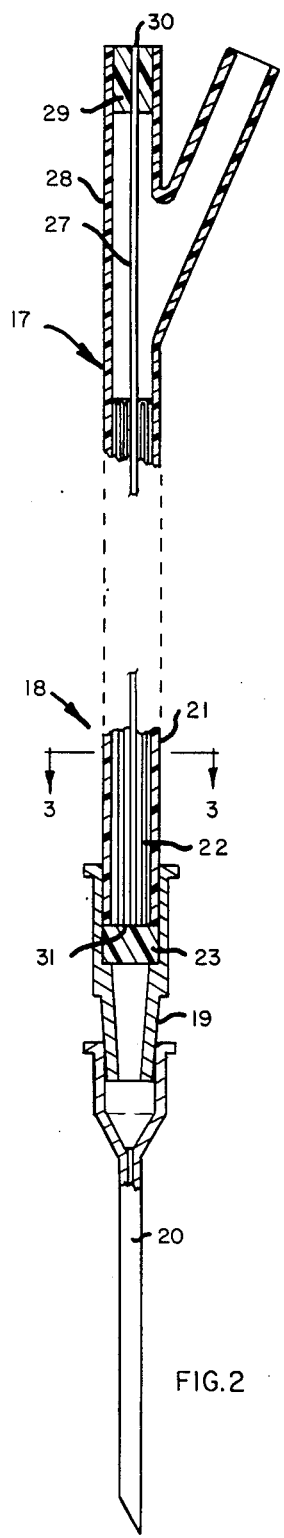
FIG. 2 is a cross-sectional view taken on line 2—2 of FIG. 1.
Figure 3:
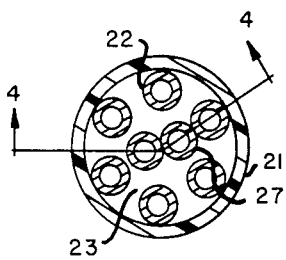
FIG. 3 is a view in cross-section taken on line 3—3 of FIG. 2.

Referring to FIGS. 2 through 4, it will be seen that filter 18 comprises a flexible nonporous tubing member 21 into which are arranged microporous hollow filter fibres 22 with the longitudinal axis of said fibres being arranged parallel to the longitudinal axis of tubing 21. A flow blocking material 23 is arranged around fibres 22 for positioning said fibres in their longitudinal direction and for blocking flow through tubular member 21 other than through said hollow fibres 21.

As shown in FIGS. 4 and 4A, the hollow fibres 22 have an opened end 2A and closed ends 25 and 26 respectively. In the embodiment of FIG. 4, the individual hollow fibres 22 are all heat sealed together to provide a closed end 25. In FIG. 4A, the hollow fibres are looped back upon themselves to provide a closed loop end 26.

In accordance with the invention, there is provided at least one gas hydrophobic permeable fibre 27 as shown in FIG. 2, which extends into tubing member 21 in the proximity of the fibres 22. One end of hydrophobic fibre 27 is in communication with the atmosphere, being held in an arm 28 of the "Y" fitting 17 by potting material 29 which can be the same material as used for potting plug 23 for holding microporous fibres 22. An open end 30 of fibre 17 extends through potting material 29 and is open to the atmosphere. The opposite end 31 of fibre 27 is sealed shut to prevent liquid passage into the interior of the fibre. Since the fibre 27 is hydrophobic, no fluid, other than gaseous materials, will pass through the material of the fibre. In this manner, gas is vented from the filter unit in the proximity of the microporous fibres 22 thus eliminating air blockage.

The tubing 21 for filter unit 18 is preferably the same type of tubing as used in I.V. administration sets, i.e., the same tubing as tubing 15. Tubing 21 can be of any length; however, the practical range would appear to be from about 3 inches to about 60 inches. Below 3 inches in length, it is believed that there would not be sufficient effective length of fibres 22 to provide adequate filtration and over 60 inches in length goes beyond the practical length of tubing extending between drip chamber 14 and needle 18. In practice, the total length of the tubing including both tubing 15 and filter 18 between drip chamber 14 and needle 18 in a typical administration set will be from about 24 inches to about 60 inches. The preferred length of the filter 18 in this arrangement, for ease of use and optimum filtration efficiency, is from about 5 inches to about 15 inches.

The effective filtration area of the microporous hollow fibres 22 is in the range of about 5 cm$^2$ to about 100 cm$^2$ with a preferred range being from about 12 cm$^2$ to about 60 cm$^2$. The effective filtration area is measured on the lumen of the fibres.

In both the arrangements of FIGS. 4 and 4A respectively, the flow of fluid can be from either direction, passing from inside to the outside of the hollow fibres in one direction and from outside to the inside of the hollow fibres in the opposite direction. Outside in flow is shown by the arrow in both FIGS. 4 and 4A.

The microporous hollow fibres 22 can be of any length up to and including the length of tube 21 with allowance being made for fittings and placement of flow blocking potting material 23. The fibres can also be relatively short in length compared to the length of tube 21 provided that sufficient filtration surface is present for the particular application. For adminsitrations with tubing 21 of the range of lengths indicated above, fibre lengths of about 1 inch to about 30 inches and preferably of about 5 inches to about 15 inches are useful provided that said fibres do not exceed the length of tubing 21.

The porosity of fibres 22 is in the microporous range of about 0.05 to about 1 microns. A preferred range is about 0.1 to about 0.45 microns.

The outside diameter for fibres 22 can be from about 0.008 inches to about 0.1 inches with a preferred outside diameter being in the range of about 0.012 inches to about 0.05 inches.

Flow blocking potting material 23 can be selected from the group of silicon, polyurethane, epoxy resins or other available adhesive with polyurethane being the currently preferred potting material.

The number of fibres 22 for standard I.V. tubing 21 is from about 2 to about 20 fibres.

The porosity of fibres 22 should be greater than about 50% with a preferred range being about 65% to 90% with the upper range of porosity being limited at a point where the fibres have no structural integrity.

Packing density of fibres 22 in tube 21 as expressed in a ratio of cross-sectional areas of fibres to cross-sectional area of the lumen of tube 21 should be less than about 60%.

While a single fibre 27 is used in a preferred form of the invention a number of such fibres can be used. The fibres can be manufactured from any gas permeable hydrophobic material of which polypropylene is preferred. The dimensions of the hydrophobic fibres 27 can be generally those of fibres 22 with a preferred inside diameter in the range of about 0.007 inches to about 0.012 inches.

It is preferred that fibre 27 extends substantially the entire length of fibres 22 to effect removal of flow blocking gas at any point along the length of such fibres 22.

While no induced pressure, other than gravitational pressure, is required for filtration of intravenous solutions in the preferred arrangement according to the invention, either positive or negative pressure can be used if desired.

In one alternate embodiment of the invention, instead of using a separate filter 18, the filter can be an integral part of the administration tube 15 itself, thus eliminating the added couplings required to place a filter inline.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description; and all changes which come within the meaning and range of equivalency of the claims are therefore intended to be embraced therein.

What is claimed is:

1. A combined inline final filter and tubing unit for the filtration and administration of intravenous fluids or the like comprising:
   a. a nonporous intravenous tubing member;
   b. microporous hollow filter fibres arranged within said tubular member parallel to the longitudinal direction thereof, said fibres being closed at one end thereof and open at the opposite ends thereof;
   c. flow blocking material arranged around said fibres for blocking flow through said tubing member other than through said hollow fibres; and,
   d. at least one hydrophobic fibre arranged to extend into said tubing member in proximity to said microporous hollow filter fibres, said hydrophobic fibre having an end thereof in communication with the atmosphere.

2. A unit according to claim 1 wherein said microporous hollow fibres are hydrophilic.

3. A unit according to claim 1 wherein said microporous hollow fibres are formed of a material comprising cellulose nitrate and cellulose acetate.

4. A unit according to claim 1 wherein said microporous hollow fibres are from about 1 inch to about 30 inches long and said flexible tubing has an internal cross-sectional area of about 5 cm$^2$ to about 100 cm$^2$.

5. A unit according to claim 3 wherein said effective filtration area is about 12 cm$^2$ to about 60 cm$^2$.

6. A unit according to claim 1 wherein said filter comprises from about 1 to about 20 of said microporous hollow fibres.

7. A unit according to claim 5 comprising about 2 to about 10 of said microporous hollow fibres.

8. A unit according to claim 1 wherein the length of said flexible nonporous tubing member is subtantially greater than the length of said fibres.

9. A unit according to claim 1 wherein said fibres have a porosity of at least greater than 50%.

10. A unit according to claim 8 wherein said porosity is from about 65% to about 90%.

11. A unit according to claim 1 further comprising coupling means to attach said tubing member to other components of an intravenous administration set.

12. A unit according to claim 1 wherein said flow blocking material is selected from the group comprising silicon, polyurethane, and epoxy resins.

13. A unit according to claim 11 wherein said resin is polyurethane.

* * * * *